United States Patent
Blitz

(10) Patent No.: US 12,251,116 B1
(45) Date of Patent: Mar. 18, 2025

(54) METHOD OF PERFORMING BUNION SURGERY

(71) Applicant: Voom Medical Devices, Inc., New York, NY (US)

(72) Inventor: Neal Blitz, New York, NY (US)

(*) Notice: Subject to any disclaimer, the term of this patent is extended or adjusted under 35 U.S.C. 154(b) by 481 days.

(21) Appl. No.: 17/842,746

(22) Filed: Jun. 16, 2022

Related U.S. Application Data

(60) Provisional application No. 63/211,165, filed on Jun. 16, 2021.

(51) Int. Cl.
*A61B 17/16* (2006.01)
*A61B 17/56* (2006.01)

(52) U.S. Cl.
CPC .......... *A61B 17/1682* (2013.01); *A61B 17/56* (2013.01); *A61B 2017/565* (2013.01)

(58) Field of Classification Search
CPC ................ A61B 17/1682; A61B 17/7291
See application file for complete search history.

(56) References Cited

U.S. PATENT DOCUMENTS

| | | | |
|---|---|---|---|
| 2011/0077656 A1* | 3/2011 | Sand | A61B 17/82 606/86 R |
| 2012/0016426 A1* | 1/2012 | Robinson | A61B 17/864 606/328 |
| 2016/0354127 A1* | 12/2016 | Lundquist | A61B 17/8061 |

\* cited by examiner

*Primary Examiner* — Andrew Yang
(74) *Attorney, Agent, or Firm* — Jonathan D. Spangler; Jay B. Bell

(57) ABSTRACT

A method of performing bunion surgery in a manner that significantly reduces or eliminates the risk of damaging the medial dorsal cutaneous (MDC) nerve while shaving or removing prominent redundant bone is described. The method of performing bunion surgery disclosed herein includes a step wherein the distal incision may be formed at an oblique angle relative to the longitudinal axis of the foot to enable insertion of the bur through the distal incision at the same or similar angle at which the incision is formed. Inserting the bur through an oblique distal incision decreases the risk of contacting the MDC nerve either during insertion or during the sweeping motion of the burr during resection of the prominent redundant bone. The oblique incision allows the bur to be placed higher on the foot, which prevents the surrounding skin from being shredded or burned by the bur during the sweeping motion.

12 Claims, 8 Drawing Sheets

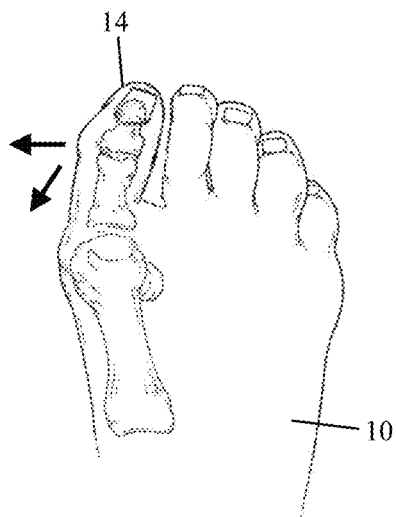
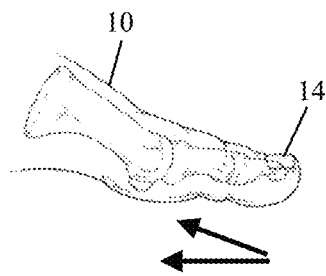
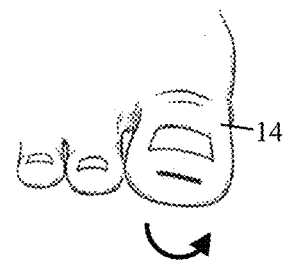
FIG. 12A  FIG. 12B  FIG. 12C
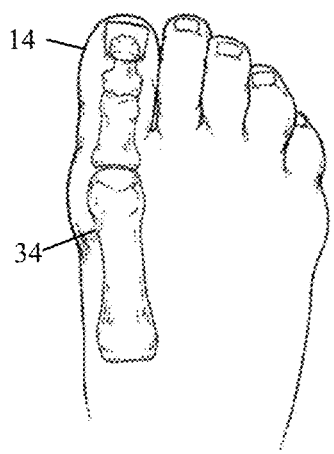
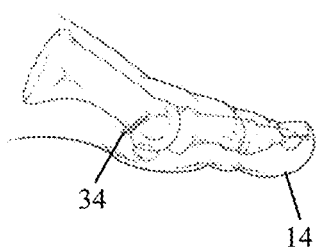
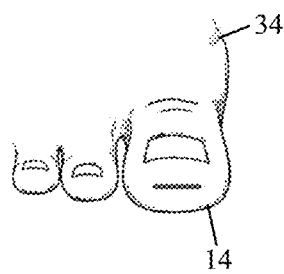
FIG. 13A  FIG. 13B  FIG. 13C

METHOD OF PERFORMING BUNION SURGERY

CROSS-REFERENCES TO RELATED APPLICATIONS

The present application is a non-provisional application claiming the benefit of priority under 35 U.S.C. § 119 (e) from commonly owned and U.S. Provisional Application Ser. No. 63/211,165 filed on Jun. 16, 2021, and entitled "METHOD OF PERFORMING BUNION SURGERY," the entire contents of which is hereby incorporated by reference into this disclosure as if set forth fully herein.

FIELD

The present disclosure relates generally to surgical methods, and more specifically to a method for shaving excess bone during minimally invasive bunion surgery.

BACKGROUND

A bunion typically appears as a bony bump near or at the base of the metatarsophalangeal (MTP) joint of the big toe. As a result, the big toe pushes against the neighboring toe, causing the MTP joint to protrude laterally. In some cases, the MTP joint of the big toe can become dislocated. If a surgical solution is sought, the metatarsal bone of the big toe is severed and realigned into proper position. Once the bone has been realigned, however, a portion of the severed metatarsal bone, also referred to as "prominent redundant bone", protrudes laterally from the foot. This prominent redundant bone portion is then cut and removed. The cut bones are then secured using any combination of fasteners, including for example screws, pins, or plates. The final result is a bunion bone that is shifted into proper alignment with the shaved bone on the side of the foot, so the inside of the foot is straight and narrow, without any bony protrusions.

Typical minimally invasive bunion surgery is performed through two tiny incisions using specialized instruments. One incision (e.g., "distal incision") is typically made at the site of the bunion (e.g., the distal end of the affected metatarsal bone), and provides an access portal for cutting and realigning the bone. The other incision (e.g., "proximal incision") is typically made near the proximal end of the affected metatarsal bone, providing an insertion trajectory for one or more fixation screws once the bone has been cut and realigned, and for a rotary bur that is typically used to shave or remove the prominent redundant bone. In current practice, both the distal incision and the proximal incision are linear horizontal incisions in that they are generally parallel to a longitudinal axis of the foot (e.g., an imaginary axis extending through the foot in a heal-to-toe direction). As used herein, the term "generally parallel" is meant to include orientations that extend in the same general direction, if not strictly parallel. The prominent redundant bone that needs to be removed after the bone is realigned is located between the two incisions but nearer to the distal portion of the affected metatarsal bone. A rotary bur spinning at high speeds is typically used during minimally invasive bunion surgery because it can be inserted through the small incision. Current practice is to insert the bur through the proximal incision.

A major nerve called the medial dorsal cutaneous nerve (referred to herein as "MDC nerve") provides sensation to the inside of the foot and the big toe and is typically located just above the 2 incisions described above. The current method of minimally invasive bunion surgery may provide a significant risk of injury to the MDC nerve. This is because current practice is to insert the rotary bur through the proximal incision, approaching the prominent redundant bone from a direction that is below and generally parallel to the MDC nerve. As the high-speed bur spins to cut the overhanging prominent redundant bone, a back-and-forth sweeping motion is also performed to ensure the bur can contact the entire surface area of the bone to be removed. The MDC nerve is in close proximity with the entire shaft of the spinning rotary bur during this motion, due to the generally parallel positioning of the bur relative to the MDC nerve. Thus, there is a relatively significant possibility of the bur becoming entangled with the MDC nerve, which may cause the nerve to sever or tear. This is known to occur in 20-30% of minimally invasive bunion surgeries, and the chance of occurrence may be higher for people that are just learning the technique.

Moreover, efforts to remove the prominent redundant bone by inserting the bur through the linear horizontal distal incision at the metatarsal neck may cause burn damage or other wound damage to the patient's skin. This so-called "zone of destruction" occurs when employing a sweeping motion on a rotary bur inserted transverse to the incision.

Thus, a need exists for a minimally invasive bunion surgical technique that provides less of a risk of damaging the MDC nerve.

SUMMARY

The present disclosure describes a method of performing bunion surgery in a manner that significantly reduces or eliminates the risk of damaging the MDC nerve during the step of shaving or removing prominent redundant bone. By way of example only, the method of performing bunion surgery disclosed herein is similar to the current state of the art described above except that in the method disclosed herein, the distal incision may be formed at an oblique angle relative to the longitudinal axis of the foot to enable insertion of the bur through the distal incision at the same or similar angle at which the incision is formed. In some embodiments, the oblique angle may be approximately 45° from proximal plantar to distal dorsal. In some embodiments, the oblique angle may be greater than 45° from proximal plantar to distal dorsal. In some embodiments, the oblique angle may be less than 45° from proximal plantar to distal dorsal. In some embodiments, the oblique angle may be within a range from 40° to 50° from proximal plantar to distal dorsal. In some embodiments, the oblique angle may be within a range from 35° to 55° from proximal plantar to distal dorsal. In some embodiments, the oblique angle may be within a range from 30° to 60° from proximal plantar to distal dorsal. In some embodiments, the oblique angle may be within a range from 25° to 65° from proximal plantar to distal dorsal.

This is advantageous because inserting the bur through an oblique distal incision decreases the risk of contacting the MDC nerve either during insertion or during the sweeping motion of the burr during resection of the prominent redundant bone. The oblique incision allows the bur to be placed higher on the foot, which prevents the surrounding skin from being shredded or burned by the bur during the sweeping motion.

In some embodiments, the first step of the method of performing bunion surgery disclosed herein is to form a pair of incisions in the patient's skin to enable access to the surgical target site (e.g., bunion). In some embodiments, one of the incisions comprises a distal incision located near the surgical target site (e.g., at the metatarsal head). In some embodiments, the distal incision is formed at an oblique angle relative to a longitudinal axis of the foot. In some embodiments, one of the incisions comprises a proximal incision. In some embodiments, the proximal incision may be formed parallel to a longitudinal axis of the foot.

In some embodiments, the next step of the method of performing bunion surgery disclosed herein comprises cutting the affected metatarsal bone and then medially translating the metatarsal head into proper alignment. In some embodiments, the instrument used to sever the metatarsal bone may be advanced to the target site through the distal incision.

In some embodiments, the next step of the method of performing bunion surgery disclosed herein is to secure the realigned bone in place using one or more fixation elements. In some embodiments, the one or more fixation elements may be advanced to the target site through the proximal incision. In some embodiments, the one or more fixation elements may be advanced to the target site through the proximal incision, distal incision, ancillary incisions, and/or percutaneous incisions.

In some embodiments, the next step of the method of performing bunion surgery disclosed herein is to cut and remove the overhanging prominent redundant bone by advancing a rotary bur through the distal incision so that the rotary bur contacts the target prominent redundant bone, and then maneuvering the bur in a sweeping motion against the target prominent redundant bone to remove a desired portion thereof. In some embodiments, the cut or shaved portion(s) of the prominent redundant bone may be removed from the target site through the distal incision.

In some embodiments, once the realigned bone has been secured with a fixation element and the target prominent redundant bone has been removed, the last step of the method of performing bunion surgery disclosed herein is to close the incisions.

In some embodiments of the method of performing bunion surgery disclosed herein, a distal incision in the form of a wedge or ellipse incision may be formed at an oblique angle relative to the longitudinal axis of the foot to (1) enable insertion of the bur through the incision at the same or similar angle at which the incision is made, and (2) create a skin flap or void that may be pulled and secured in various directions to enable additional correction of the big toe position (e.g., both adduction or toward the body's midline, and valgus or away from the body's midline) of the bunion deformity.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIGS. 12A-12C are top, side, and front views, respectively, of an example of a patient's foot illustrating a second step in a method of correcting big toe alignment in a bunion patient, according to some embodiments; and FIGS. 13A-13C are top, side, and front views, respectively, of an example of a patient's foot illustrating a third step in a method of correcting big toe alignment in a bunion patient, according to some embodiments.

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. The method of performing bunion surgery disclosed herein boasts a variety of inventive features and components that warrant patent protection, both individually and in combination.

Figure 1:
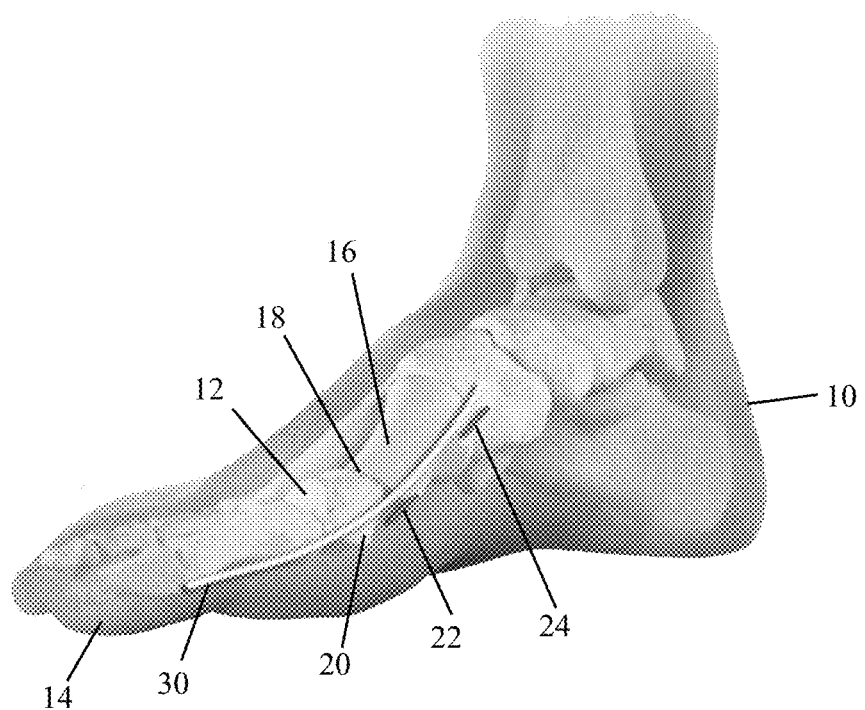
FIG. 1 is a perspective view of a foot illustrating in particular the placement of several incisions for accessing a surgical target site, according to some embodiments.
Figure 2A:
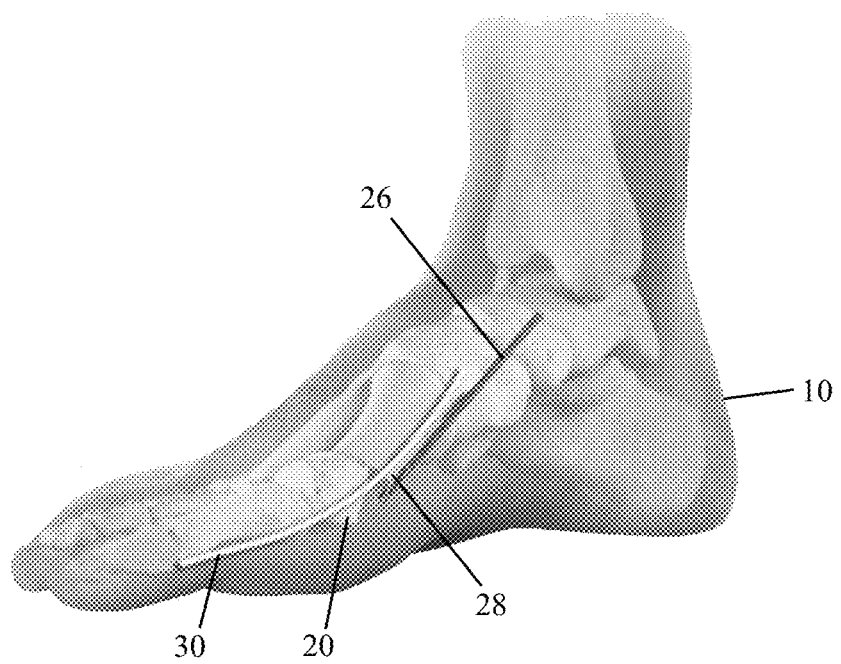
FIG. 2A is a perspective view of the foot of FIG. 1, illustrating in particular a prior art insertion trajectory of a rotary bur, according to some embodiments.
Figure 2B:
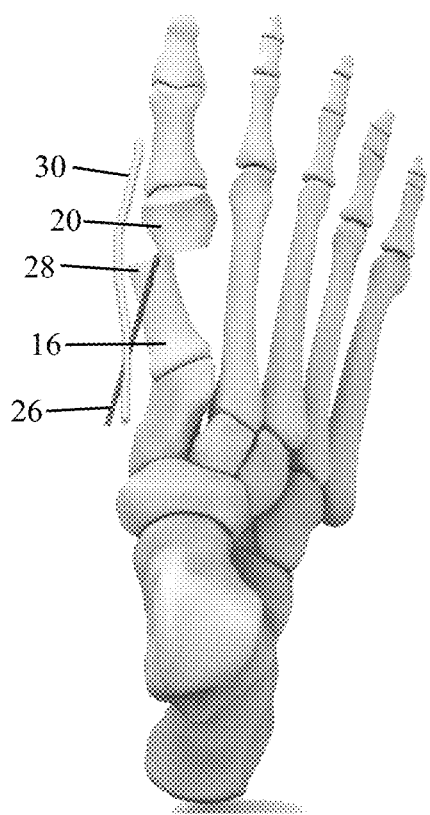
FIG. 2B is a top plan view of the foot and prior art trajectory of a rotary bur of FIG. 2A, according to some embodiments.
Figure 2C:
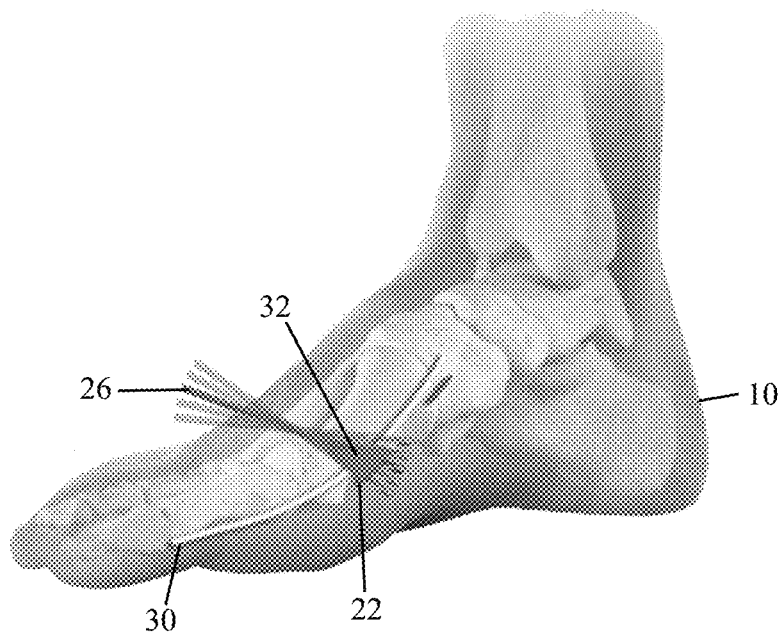
FIG. 2C is a perspective view of the foot of FIG. 1, illustrating in particular a zone of destruction that may occur if a rotary bur is inserted through a prior art distal incision, according to some embodiments.
Figure 3:
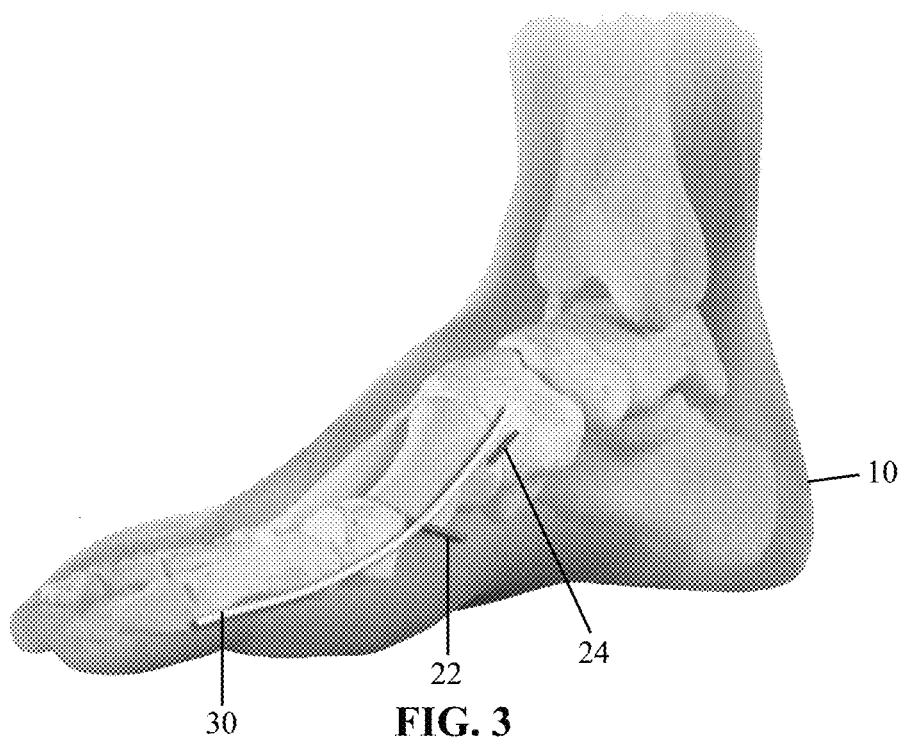
FIG. 3 is another perspective view of a foot illustrating in particular an alternative placement of several incisions for accessing a surgical target site, according to some embodiments.

FIGS. 1-2C illustrate aspects of a typical bunion correction surgery, as commonly performed using prior art techniques. By way of example only, FIGS. 1-2C illustrate an example of a foot 10 with a bunion growth in the metatarsophalangeal (MTP) joint 12 of the big toe 14. At this point in the procedure, the affected metatarsal bone 16 has been cut 18, and the metatarsal head 20 has been medially translated and fixed in proper alignment using one or more fixation members (not shown), for example a fixation member as shown and described in commonly owned U.S. patent application Ser. No. 16/571,042, filed on Sep. 13, 2019 and entitled "Orthopedic Bone Screw" (now issued as U.S. Pat. No. 11,045,239), which is hereby incorporated by reference as if set forth fully herein.

Typical minimally invasive bunion surgery is performed through two tiny incisions using specialized instruments. A first or distal incision 22 is typically made at or near the site of the bunion (e.g., metatarsal head 20), and provides an access portal for cutting and realigning the bone. A second or proximal incision 24 is typically made near the proximal end of the affected metatarsal bone 16, providing an insertion trajectory for one or more fixation members once the bone has been cut and realigned, and for a rotary bur 26 that is typically used to shave or remove the prominent redundant bone 28. In current practice, both the distal incision 22 and the proximal incision 24 are linear horizontal incisions in that they are generally parallel to the longitudinal axis of the foot. The prominent redundant bone 28 that needs to be removed after the bone is realigned is located between the two incisions but nearer to the distal portion of the affected metatarsal bone. A rotary bur 26 spinning at high speeds is typically used during minimally invasive bunion surgery because it can be inserted through the small incisions. Current practice is to insert the bur 26 through the proximal incision 24.

A major nerve called the medial dorsal cutaneous nerve 30 (referred to herein as "MDC nerve 30") provides sensation to the inside of the foot and the big toe, and is typically located just above the distal and proximal incisions 22, 24. Current practice is to insert the rotary bur 26 through the proximal incision 24, approaching the prominent redundant bone 28 from a direction that is below and generally parallel to the MDC nerve 30, as shown by way of example in FIGS. 2A-2B. However, this current practice may provide a significant risk of injury to the MDC nerve 30. As the high-speed bur 26 spins to cut the overhanging prominent redundant bone 28, a back-and-forth sweeping motion is also performed to ensure the bur 26 can contact the entire surface area of the bone to be removed. The MDC nerve 30 is in close proximity with the entire shaft of the spinning rotary bur 26 during this motion, due to the generally parallel positioning of the bur 26 relative to the MDC nerve 30. Thus, there may be a relatively significant possibility of the bur 26 becoming entangled with the MDC nerve 30, which may cause the nerve to sever or tear.

As illustrated by way of example only in FIG. 2C, efforts to remove the prominent redundant bone by inserting the bur 26 through the linear horizontal distal incision 22 at the metatarsal neck may cause burn damage or other wound damage to the patient's skin. This so-called "zone of destruction" 32 occurs when employing a sweeping motion on a rotary bur inserted transverse to the direction or angle of the incision 22.

Thus, as illustrated by way of example only in FIGS. 3-8, in some embodiments of the method of performing bunion surgery disclosed herein, the distal incision 22 may be formed at an oblique angle relative to the longitudinal axis of the foot to enable insertion of the bur 26 through the incision 22 at the same or similar angle at which the incision is made. In some embodiments, the oblique angle may be approximately 45° from proximal plantar to distal dorsal. In some embodiments, the oblique angle may be greater than 45° from proximal plantar to distal dorsal. In some embodiments, the oblique angle may be less than 45° from proximal plantar to distal dorsal. In some embodiments, the oblique angle may be within a range from 40° to 50° from proximal plantar to distal dorsal. In some embodiments, the oblique angle may be within a range from 35° to 55° from proximal plantar to distal dorsal. In some embodiments, the oblique angle may be within a range from 30° to 60° from proximal plantar to distal dorsal. In some embodiments, the oblique angle may be within a range from 25° to 65° from proximal plantar to distal dorsal.

Figure 4:
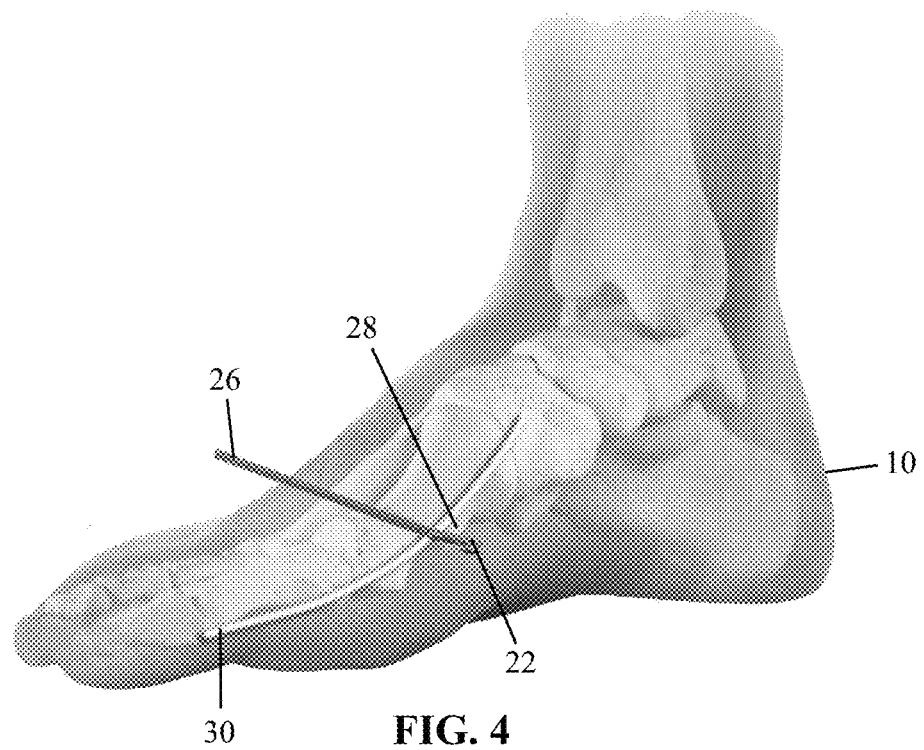
FIG. 4 is a perspective view of the foot of FIG. 3, illustrating in particular the insertion of a rotary bur through a distal incision, according to some embodiments.
Figure 5:
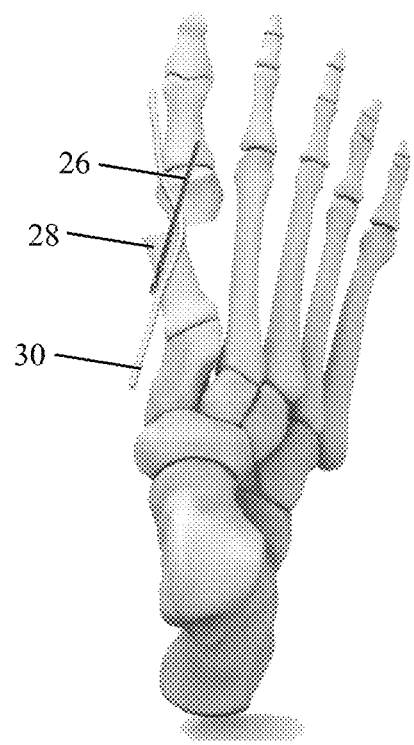
FIG. 5 is a top plan view of the foot of FIG. 4, illustrating in particular the insertion of a rotary bur through the distal incision, according to some embodiments.
Figure 6:
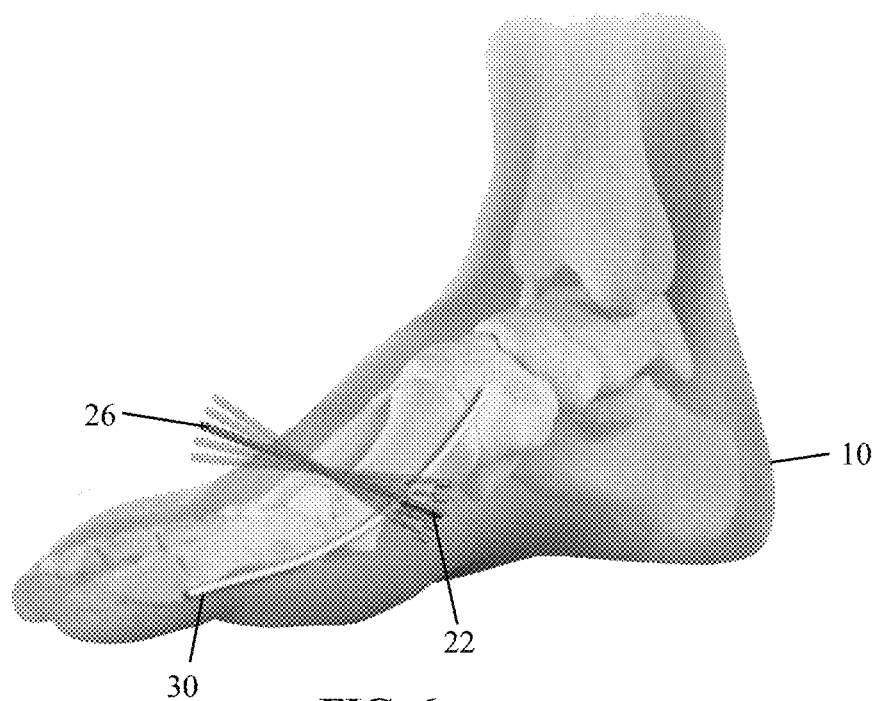
FIG. 6 is a perspective view of the foot of FIG. 4, illustrating in particular the sweeping motion of the rotary bur, according to some embodiments.
Figure 7:
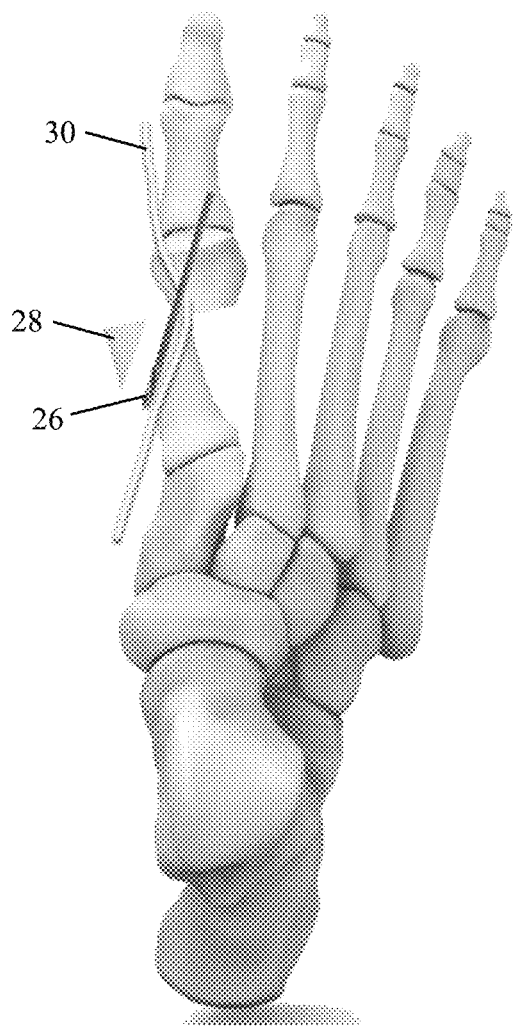
FIGS. 7-8 are top plan views of the foot of FIG. 4, illustrating in particular the cut portion of prominent redundant bone, according to some embodiments.
Figure 8:
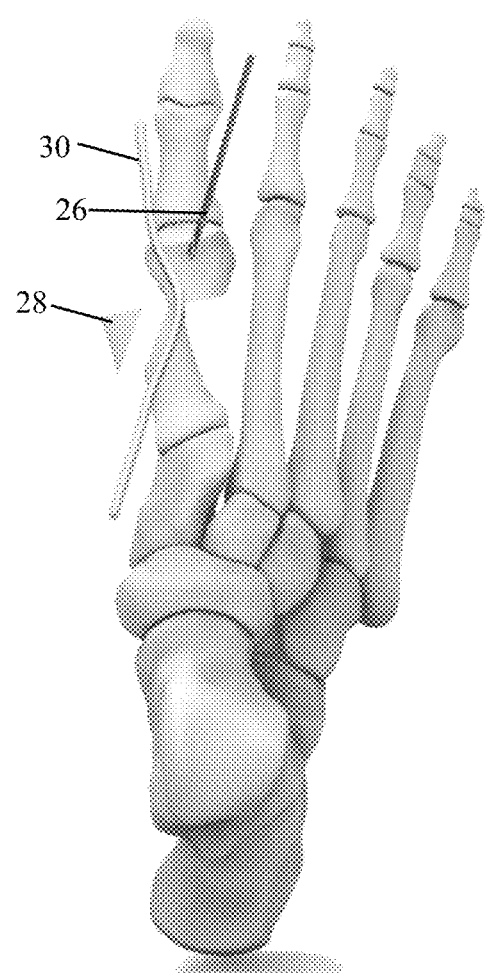

As illustrated by way of example only in FIGS. 4-6, inserting the bur 26 through an oblique distal incision 22 decreases the risk of contacting the MDC nerve 30 either during insertion or during the sweeping motion of the burr 26 during resection of the prominent redundant bone 28. The oblique incision 22 allows the bur 26 to be placed higher on the foot, which prevents the surrounding skin from being shredded or burned by the bur 26 during the sweeping motion.

Figure 9:
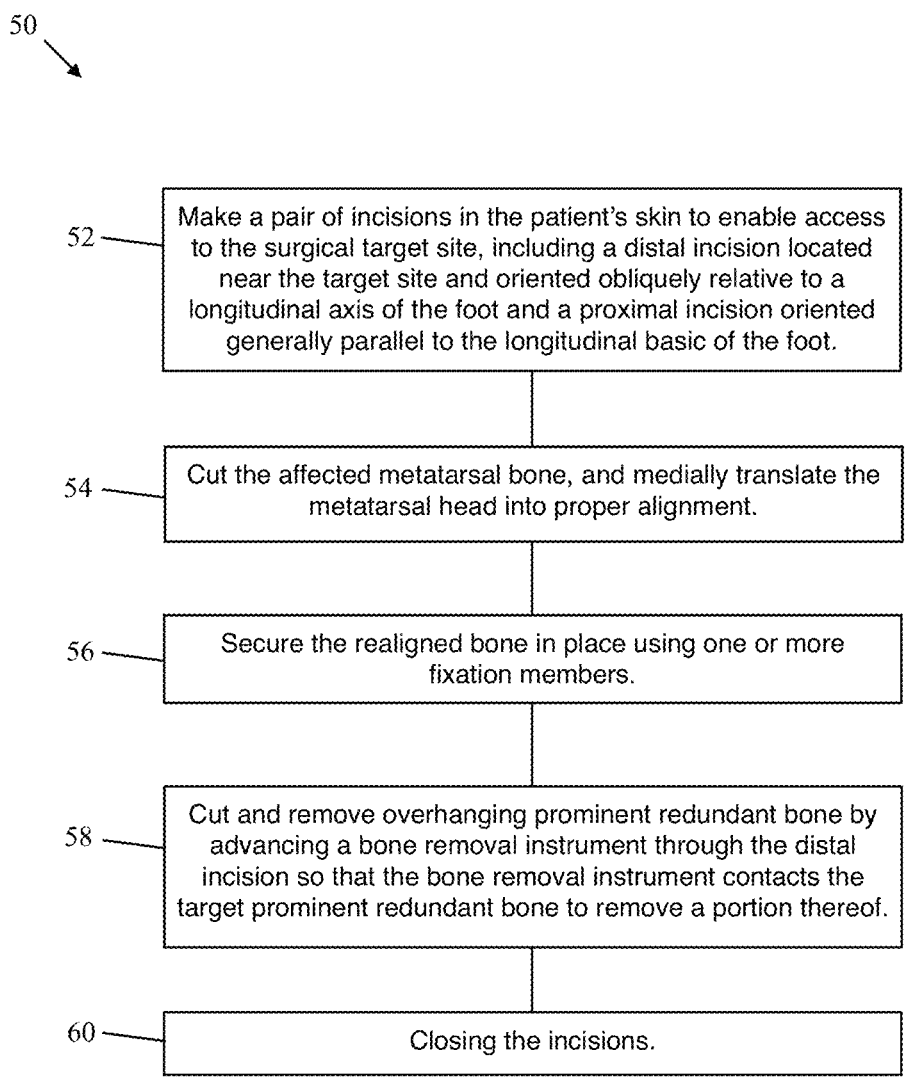
FIG. 9 is a flowchart depicting several steps of a method of performing bunion surgery, according to some embodiments.

FIG. 9 is a flowchart describing the various steps of one example of a method 50 of performing bunion surgery using the novel approach to the prominent redundant bone, disclosed herein according to some embodiments. In some embodiments, the first step 52 of the method 50 is to form a pair of incisions in the patient's skin to enable access to the surgical target site (e.g., bunion). In some embodiments, one of the incisions comprises a distal incision 22 located near the surgical target site (e.g., at the metatarsal head 20). In some embodiments, the distal incision 22 is formed at an oblique angle relative to a longitudinal axis of the foot 10. In some embodiments, one of the incisions comprises a proximal incision 24. In some embodiments, the proximal incision 24 may be formed parallel to a longitudinal axis of the foot 10.

In some embodiments, the next step 54 of the method 50 comprises cutting the affected metatarsal bone 16 and then medially translating the metatarsal head 20 into proper alignment. In some embodiments, the instrument used to sever the metatarsal bone 16 may be advanced to the target site through the distal incision 22.

In some embodiments, the next step 56 of the method 50 is to secure the realigned bone in place using one or more fixation elements. In some embodiments, the one or more fixation elements may be advanced to the target site through the proximal incision 24. In some embodiments, the one or more fixation elements may be advanced to the target site through the proximal incision 24, distal incision 22, ancillary incisions, and/or percutaneous incisions.

In some embodiments, the next step 58 of the method 50 is to cut and remove the overhanging prominent redundant bone 28 by advancing a rotary bur 26 through the distal incision 22 so that the rotary bur 26 contacts the target prominent redundant bone 28, and then maneuvering the bur 26 in a sweeping motion against the target prominent redundant bone 28 to remove a desired portion thereof. In some embodiments, the cut or shaved portion(s) of the prominent redundant bone 28 may be removed from the target site through the distal incision 22.

In some embodiments, once the realigned bone has been secured with a fixation element and the target prominent redundant bone 28 has been removed, the last step 60 of the method 50 is to close the incisions 22, 24.

Figure 10:
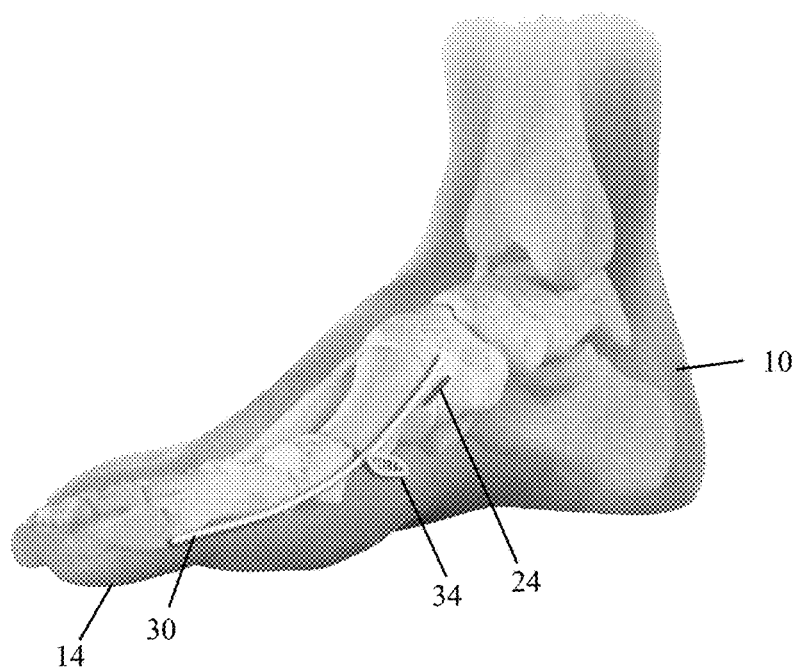
FIG. 10 is another perspective view of a foot illustrating in particular an alternative placement of several incisions for accessing a surgical target site, according to some embodiments.

As illustrated by way of example only in FIG. 10, in some embodiments of the method of performing bunion surgery disclosed herein, a distal incision 34 in the form of a wedge or ellipse incision may be formed (in lieu of the linear oblique distal incision 22 described above) at an oblique angle relative to the longitudinal axis of the foot to (1) enable insertion of the bur 26 through the incision 22 at the same or similar angle at which the incision is made, and (2) create a skin flap or void that may be pulled and secured in various directions to enable additional correction of the big toe 14 position (e.g., both adduction or toward the body's midline, and valgus or away from the body's midline) of the bunion deformity. In some embodiments, the big toe 14 position may be corrected using one or more additional skin flaps created near the distal incision 22 or distal incision 34.

Figure 11A:
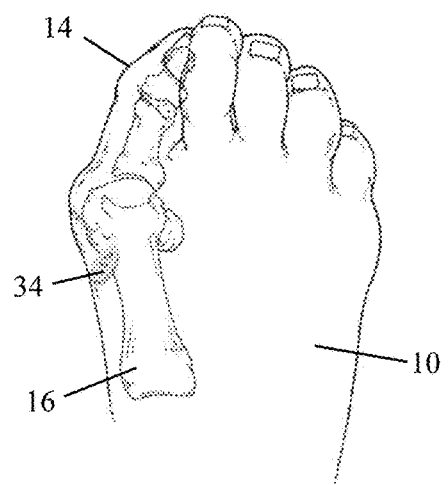
FIGS. 11A-11C are top, side, and front views, respectively, of an example of a patient's foot illustrating a first step in a method of correcting big toe alignment in a bunion patient, according to some embodiments.
Figure 11B:
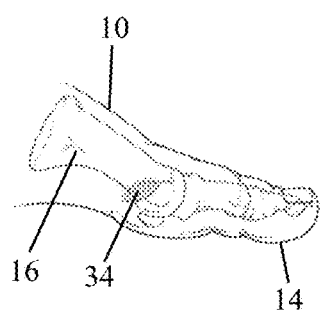
Figure 11C:
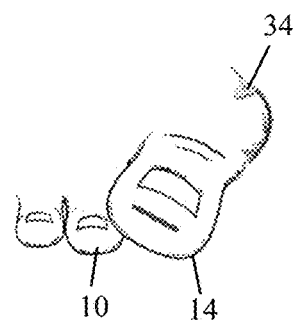

By way of example only, FIGS. 11A-13C illustrate an example method of correcting big toe deformity by using an elliptical or wedge-shaped incision 34 described above, according to some embodiments. For example, FIGS. 11A-11C illustrate top, side, and front views of an example patient's foot 10 having a big toe 14 deformity due to a bunion. Similar to the illustration of FIG. 10, an elliptical or wedge-shaped incision 34 has been made at an oblique angle relative to the longitudinal axis of the foot near the distal end of the metatarsal bone 16. In some embodiments, the incision 34 may comprise a complete removal of a patch of skin. In some embodiments, the incision 34 may leave at least a portion of a flap of skin. After performing the bunion correction procedure described above, the big toe 14 positioning may be corrected by pulling on a distal edge of the elliptical incision 34 or flap portion in a generally proximal oblique direction (e.g., transverse to the angle of the incision). In some embodiments, this may result in big toe repositioning in multiple planes. In some embodiments, this may result in a triplanar repositioning of the big toe 14, as illustrated in FIGS. 12A-12C. In some embodiments, the big toe 14 may be corrected in a single plane. For example, as illustrated in FIGS. 12A-12B, pulling on the distal incision 34 may cause the big toe 14 to be repositioned laterally outward (e.g. away from the midline of the foot) and obliquely backward. As illustrated in FIG. 12C, pulling on the distal incision 34 may cause the big toe 14 to be repositioned rotationally counterclockwise (e.g., for a right foot) or rotationally clockwise (e.g., for a left foot) depending on the foot being treated. Once the big toe 14 has been realigned, the incision 34 may be closed, as illustrated by way of example only in FIGS. 13A-13C.

What is claimed is:

1. A method of performing surgery on a patient having an affected foot including a surgical target site comprising a bunion at or near a base of an affected metatarsal bone of the big toe of the patient's foot, comprising the steps of:
    positioning the patient's affected foot in an operable position on an operating table;
    making a first incision near a metatarsal head at the distal end of the affected metatarsal bone, the first incision being formed at an oblique angle relative to a longitudinal axis of the affected foot;
    making a second incision near the proximal end of the affected metatarsal bone, the second incision formed parallel to the longitudinal axis of the affected foot;
    advancing a cutting instrument through the first incision to cut the affected metatarsal bone;
    medially translating the metatarsal head into a corrective alignment;
    securing the realigned bone in place by advancing one or more fixation members toward the surgical target site;
    cutting and removing overhanging prominent redundant bone by advancing a bone removal instrument through the first incision so that the bone removal instrument contacts the overhanging prominent redundant bone;
    removing the bone removal instrument from the first incision; and
    closing the first and second incisions.

2. The method of claim 1, wherein the bone removal instrument is a rotary bur.

3. The method of claim 1, wherein the one or more fixation members are advanced toward the surgical target site through at least one the first incision, the second incision, an ancillary incision, and a percutaneous incision.

4. The method of claim 1, wherein the first incision is a linear incision.

5. The method of claim 1, wherein the first incision is a wedge-shaped incision.

6. The method of claim 1, wherein the first incision is an elliptical incision.

7. The method of claim 1, wherein the oblique angle is approximately 45° from proximal plantar to distal dorsal.

8. The method of claim 1, wherein the oblique angle is one of greater than 45° from proximal plantar to distal dorsal and less than 45° from proximal plantar to distal dorsal.

9. The method of claim 1, wherein the oblique angle is within a range from 40° to 50° from proximal plantar to distal dorsal.

10. The method of claim 1, wherein the oblique angle is within a range from 35° to 55° from proximal plantar to distal dorsal.

11. The method of claim 1, wherein the oblique angle is within a range from 30° to 60° from proximal plantar to distal dorsal.

12. The method of claim 1, wherein the oblique angle is within a range from 25° to 65° from proximal plantar to distal dorsal.

* * * * *